(12) United States Patent
Wannerberger et al.

(10) Patent No.: US 7,018,653 B2
(45) Date of Patent: *Mar. 28, 2006

(54) METHOD FOR PREPARING SOLID DOSAGE FORM OF DESMOPRESSIN

(75) Inventors: Kristen Wannerberger, Lund (SE); Hans Lindner, Frederiksberg (DK); Lars-Erik Olsson, Malmo (SE); Ann Elisabeth Svensson, Lomma (SE)

(73) Assignee: Ferring B.V., Hoofddorp (NL)

( * ) Notice: Subject to any disclaimer, the term of this patent is extended or adjusted under 35 U.S.C. 154(b) by 179 days.

This patent is subject to a terminal disclaimer.

(21) Appl. No.: 10/746,254

(22) Filed: Dec. 29, 2003

(65) Prior Publication Data

US 2005/0158378 A1    Jul. 21, 2005

(51) Int. Cl.
*A61K 9/26*    (2006.01)

(52) U.S. Cl. ............. 424/470; 424/464; 424/465; 424/468

(58) Field of Classification Search ............. 424/470, 424/464, 465, 468
See application file for complete search history.

(56) References Cited

U.S. PATENT DOCUMENTS

| | | | | |
|---|---|---|---|---|
| 4,675,188 | A | * | 6/1987 | Chu ................. 424/602 |
| 4,820,627 | A | * | 4/1989 | McGeehan ............. 435/4 |
| 5,047,398 | A | * | 9/1991 | Hagstam et al. ........ 514/15 |
| 2002/0028240 | A1 | | 3/2002 | Sawada et al. |
| 2002/0122817 | A1 | * | 9/2002 | Gabel et al. ........... 424/450 |
| 2003/0091637 | A1 | | 5/2003 | Petereit et al. |
| 2003/0175214 | A1 | | 9/2003 | Staniforth et al. |
| 2003/0185764 | A1 | | 10/2003 | Staniforth et al. |
| 2004/0220080 | A1 | | 11/2004 | Lomryd et al. |
| 2005/0019392 | A1 | | 1/2005 | Lomryd et al. |

FOREIGN PATENT DOCUMENTS

| | | |
|---|---|---|
| EP | 0 752 877 B1 | 7/2000 |
| EP | 0 710 122 B1 | 12/2001 |
| EP | 1 255 557 A1 | 11/2002 |
| WO | WO 95/18602 | 7/1995 |
| WO | WO 97/15297 | 5/1997 |
| WO | WO 97/23485 A1 | 7/1997 |
| WO | WO 00/59423 A | 10/2000 |
| WO | WO 01/78694 A2 | 10/2001 |
| WO | WO 01/78695 A2 | 10/2001 |
| WO | WO 01/78696 A2 | 10/2001 |
| WO | WO 01/82906 A1 | 11/2001 |
| WO | WO 02/00197 A1 | 1/2002 |
| WO | WO 03/094886 A2 | 11/2003 |

OTHER PUBLICATIONS

"Current Issues and Troubleshooting Fluid Bed Granulation," May 1998, Pharmaceutical Technology Europe,http://www.niroinc.com/html/pharma/phpdfs/niroreprint2.pdf.*

Robert O. Williams III et al.; "Compaction Properties of Microscrystalline Cellulose and Sodium Sulfathiazole in Combination with Talc or Magnesium Stearate", Journal of Pharmaceutical Sciences, vol. 78, No. 12, Dec. 1989, pp. 1025-1034.

"Pharmaceutical Dosage Forms: Tablets"; vol. 1, pp. 297-298, H.A. Lieberman et al., New York & Basel, 1989.

"Pharmaceutical Dosage Forms: Parenteral Medications", vol. 3, pp. 27-29, H.A. Lieberman et al., New York & Basel, 1990.

"Pharmaceutics—The Science of Dosage Form Design", pp. 625-627, M.E. Aulton et al., Edinburgh, London, Melbourne & New York, 1988.

"Handbook of Pharmaceutical Excipients", Ed. A.H. Kibble, 3$^{rd}$ Ed., American Pharmaceutical Assocation, USAS and Pharmaceutical Press UK 2000.

N.A. Armstrong: "Tabletting", Pharmaceutics—The Science of Dosage Form Design, pp. 647-668, 1988.

* cited by examiner

*Primary Examiner*—Thurman K. Page
*Assistant Examiner*—Pili A Hawes
(74) *Attorney, Agent, or Firm*—Foley & Lardner LLP

(57) ABSTRACT

The present invention relates to a novel method for the preparation of a solid dosage form of desmopressin, or a pharmaceutically acceptable salt thereof, comprising providing a desmopressin containing granulate suitable for compression to a pharmaceutically acceptable tablet, as well as to solid dosage forms, preferably tablets, obtainable by said method.

14 Claims, No Drawings

METHOD FOR PREPARING SOLID DOSAGE FORM OF DESMOPRESSIN

FIELD OF THE INVENTION

The present invention relates to a novel method for the preparation of a solid dosage form of desmopressin, or a pharmaceutically acceptable salt thereof, as well as to solid dosage forms, preferably tablets, obtainable by said method.

BACKGROUND

Desmopressin, also known as dDAVP, is a nonapeptide and the therapeutically active ingredient (as the acetate salt) in the pharmaceutical product Minirin®, which is marketed inter alia as a nasal spray and a tablet formulation. Desmopressin is primarily used in the treatment of primary nocturnal enuresis, i.e. bedwetting, in children, but it is approved also for the treatment of nocturia and diabetes insipidus. The first market introduction of the tablet formulation was in Sweden in 1987. The composition of the marketed tablet form of desmopressin has remained the same to date.

The tablet form of desmopressin was first disclosed as set forth in the U.S. Pat. No. 5,047,398. The subsequently issued marketing authorisations relate to a tablet where i.a. the mannitol, talc and cellulose components exemplified in U.S. Pat. No. 5,047,398 are replaced with potato starch. In addition to desmopressin acetate and potato starch, the present tablet components are lactose, polyvinylpyrrolidone (PVP) and magnesium stearate that together form a homogeneous tablet compressed from a granulate. This composition is inter alia disclosed in the publication WO 03/94886 A1 (see page 28).

Since desmopressin is a nonapeptide containing a disulfide bond, its stability must always be considered. Representative publications addressing the problem of the stability of desmopressin in pharmaceutical formulations are EP 1255557 A1, EP 752877 A1 and EP 710122 A1.

Desmopressin containing granulate has to date been prepared in a wet granulation process involving a sequence of several sieving and mixing steps performed at ambient temperature and humidity followed by drying (cf. example 1 herein). One of the objectives of that procedure is to keep shearing forces that desmopressin may be subjected to at a minimum level. The main disadvantages of said procedure is that it is rather time-consuming and labor intensive.

The publication WO 97/15297 A1 (examples 6 and 10) discloses a wet granulation method for the preparation of a buccal delivery system for desmopressin.

As a mixture of water and ethanol is used as the granulation liquid in the prior art granulate preparation, the resulting tablet inevitably contains solvent residues, typically 5–6% of water and 0.1% of ethanol (percentage by weight). Complete removal of solvent residues by drying is impractical, as conditions for complete drying of solid dosage forms tend to be either too costly in industrial scale or potentially thermally damaging to the desmopressin. The primary purpose of the added ethanol is to shorten the time of drying (via an azeotrope).

It is an objective of the present invention to overcome the aforementioned disadvantages.

DISCLOSURE OF THE INVENTION

The present invention relates to a method for the preparation of a solid dosage form of desmopressin, or a pharmaceutically acceptable salt thereof, comprising providing a desmopressin containing granulate suitable for compression to a pharmaceutically acceptable tablet, wherein preparation of said granulate comprises fluid bed granulation processing within an apparatus adapted therefor. More specifically, said processing comprises providing conditions to provide mixing and shearing action. Said conditions typically comprise adjusting fluidising air flow and processing temperature and time.

Standard literature (see "*Pharmaceutical Dosage Forms; Tablets*", vol. 1, pages 297–298, Eds. H. A. Lieberman, L. Lachman and J. B. Schwartz, Marcel Dekker, Inc., New York and Basel, 1989) teaches that the conditions involved in fluid bed granulation may be harmful e.g. to enzymes. More specifically, the heat and moisture combined with the circulating air and particles in a fluid bed granulation process generate significant shearing and abrasion forces with the purpose of providing a granulate having flow properties ideal for tablet compression at industrial scale and speed. Such flow properties are due to the resulting smooth surface structure of the granulate subjected to said shearing and abrasion forces.

It is a surprising observation that a molecule as sensitive as desmopressin can withstand the processing conditions of fluid bed granulation. The most significant advantages of the method of the present invention are the short processing time compared to conventional wet granulation, and the excellent flow properties for compression of the resulting granulate.

Fluid bed granulation per se is a conventional technology, and it is extensively disclosed in various standard literature, such as "*Pharmaceutical Dosage Forms; Tablets*", vol. 3, pages 27–29, Eds. H. A. Lieberman, L. Lachman and J. B. Schwartz, Marcel Dekker, Inc., New York and Basel, 1990) and "*Pharmaceutics—The science of dosage form design*", pages 625–627; Ed. M. E. Aulton, Churchill Livingstone, Edinburgh, London, Melbourne and New York 1988. The proper selection of the general equipment set up & processing conditions is therefore within the capacity of a person skilled in the art of manufacturing pharmaceutical formulations. Examples of commercial providers of apparatus adapted for fluid bed granulation are Aeromatic-Fielder AG, CH (Strea series) and Glatt GmbH, DE.

In a preferred embodiment of the present method, said desmopressin containing granulate is prepared by a process comprising the steps of:
  i) providing a powder comprising, or consisting of, at least one excipient, carrier or diluent, or mixture thereof;
  ii) providing a granulation liquid containing a solvent and desmopressin, or a pharmaceutically acceptable salt thereof, and optionally a binder; and
  iii) contacting said granulation liquid, preferably by spraying, with said powder within said apparatus, wherein the fluidising air flow and processing temperature and time are simultaneously, and optionally also after said contacting is completed, adjusted to provide said mixing and shearing action.

The processing conditions of fluid bed granulation usually also provide drying while the fluidisation is ongoing, i.e. also during said step iii). Continued processing conditions after said contacting thus provide further drying in addition to the mixing and shearing action. As an example, a spraying operation in fluid bed granulation is typically performed at a constant spraying rate over a time period of from 10 to 60 minutes. Optionally, the spraying is followed by continued processing conditions for 10 to 240 minutes if further drying, mixing and/or shearing action is desired.

Said solvent is preferably water, which is a particularly advantageous aspect of the present invention. It is noteworthy that the use of water as sole solvent nevertheless keeps the time of drying short, whereas explosion risks and organic solvent exposure are reduced while providing a granulate of required quality. In addition, the granulation process is simplified by removing a component.

Fluidising air flow refers to an air flow that is sufficient to accomplish fluidisation of the powder and resulting granulate within the fluid bed-granulation apparatus. The required air flow depends upon several parameters, including particle size and density. As a non-limiting example, the air flow may be in the range of from 10 to 2 500 $m^3/h$, preferably from 20 to 1 500 $m^3/h$. Different operating scales will inherently require somewhat different fluidising air flows. Selecting an optimal flow for the operating scale in question is not an impractical burden for a person skilled in the art, as the machinery per se required in the practising of the present invention is commercially available and thus of a conventional nature.

Said processing temperature is typically in the range of from 25 to 80° C., preferably from 30 to 60° C. Temperature ranges of from 35 to 55° C. and from 40 to 50° C. are also conceivable.

It is preferred that said processing time is in the range of from 10 to 240 minutes. For practical purposes, the process is typically regarded as complete when the formed granulate, which is also dried during the process, reaches a water content that is essentially equal to that of said powder comprising excipient, carrier or diluent.

In many cases the terms excipient, diluent and carrier can be used interchangeably, and they may even refer to one and the same substance, or to a mixture of similar such substances. The proper use and understanding of these terms is well known to a person skilled in the art.

In the present method it is preferred that said excipient, carrier or diluent is selected from cellulose, starch and lactose. As used herein, the term cellulose includes, taken alone or in mixture, neat cellulose, microcrystalline cellulose, carboxymethyl cellulose, hydroxypropyl methylcellulose as well as other variants thereof that may be employed in pharmaceutical formulations. As used herein, the term starch includes, taken alone or in mixture, potato starch, wheat starch, corn starch, rice starch and sheared and/or acid-hydrolysed variants of the aforementioned starches as well as other variants of starch that are typical in pharmaceutical formulations. The lactose type used is preferably lactose-α-monohydrate.

As indicated above the present solid dosage form may optionally comprise at least one further additive typically selected from a disintegrating agent, binder, lubricant, flavoring agent, preservative, colorant and any suitable mixture thereof. Examples of additives that may be considered in practising the present invention are found in "*Handbook of Pharmaceutical Excipients*"; Ed. A. H. Kibbe, $3^{rd}$ Ed., American Pharmaceutical Association, USA and Pharmaceutical Press UK, 2000.

In a preferred embodiment of the present method, said desmopressin containing granulate is compressed to a tablet, preferably in a process where a lubricant is added to said granulate before compression thereof.

Said lubricant is typically selected from a group consisting of stearic acid, salts or esters of stearic acid, hydrogenated vegetable oils, magnesium oxide, polyethylene glycol, sodium lauryl sulphate and talc, and mixtures thereof. Preferably said lubricant is selected from magnesium stearate, calcium stearate, zinc stearate, glyceryl palmitostearate and sodium stearyl fumarate, and mixtures thereof. Magnesium stearate is most preferred. The content of lubricant is typically from 0.05 to 1.0, preferably from 0.25 to 0.50, percent by weight of each unit of solid dosage form.

The practising of the present method preferably includes a binder, e.g. PVP. Typically an amount of binder of from 1 to 6 percent by weight of each unit of solid dosage form is employed.

In the most preferred embodiment said solid dosage form lacks an enteric coating. By avoiding an enteric coating the preparation of the solid dosage form of the present invention is further simplified.

The solid dosage form as eventually prepared preferably lacks an agent that exerts buffering capacity at a pH of from 2 to 6.

The method of the present invention most preferably provides an amount of desmopressin acetate of from 20 to 600 μg per unit of said solid dosage form.

Said solid dosage form is preferably selected from a group consisting of tablets, granulate powder, lozenge, cachet, and wafer sheet. A tablet is most preferred.

The present pharmaceutical composition in a solid dosage form is typically a perorally available tablet. A tablet may be manufactured by compression of a granulate by procedures well established in the art. Examples of suitable tablet compressing equipment are rotary presses provided by Elizabeth-Hata International, USA, and Courtoy NV, BE. For a comprehensive overview of pharmaceutical tablet manufacturing, see "*Tabletting*" (by N. A. Armstrong) in the aforementioned "*Pharmaceutics—The science of dosage form design*", pages 647–668.

Accordingly, a further aspect of the present invention relates to a solid dosage form, preferably a tablet, that is obtainable by a method as defined above, both in general and as outlined in the specific embodiments.

The following illustrates the present invention in more detail. It shall not be construed as a limitation of how the invention may be practised.

EXPERIMENTAL

Example 1

(Prior Art) Preparation of a Tablet Containing Desmopressin Acetate Via Wet Granulation Lactose (900 g, Pharmatose 150M; provided by DMV, NL) and potato starch (550 g, AmylSolVät; provided by Lyckeby Stärkelse AB, SE) are mixed in a planetary mixer for 15 minutes at room temperature and sieved through a 1 mm sieve. A granulation liquid consisting of water (75 ml) and PVP (13.8 g, Kollidon® 25; provided by BASF GmbH, DE) is prepared, to which desmopressin acetate (0.75 g; provided by PolyPeptide Laboratories AB, SE) and ethanol (225 g) are added. The granulation liquid is then gradually added to the lactose/starch mixture during mixing for 20 minutes, followed by further mixing for 10 minutes at room temperature. After sieving (1.4 mm), drying for about 20 hours at 40° C. and further sieving (1.4 mm), the obtained granulate is admixed with magnesium stearate (11.3 g, 1.0 mm sieved; provided by Peter Greven NV, NL) and subsequently compressed to 7500 tablets using a single punch tablet compression machine (Fette Exacta 1). A typical prepared tablet for commercial use contains 0.1 mg of desmopressin acetate and is white, convex and oval (6.8×9.6 mm) with a thickness of 3–4 mm and a target weight of 192 mg. It has a smooth surface without scratches or chipped edges, and shows no tendencies to lamination (so-called capping).

Example 2

Preparation of a Tablet Containing Desmopressin Acetate Via Fluid Bed Granulation Lactose (476.6 g, Granulac 140; provided by Meggle AG, DE) and potato starch (294.6 g, M14; provided by KMC, DK) are fed to a fluid bed granulation apparatus (Strea 1; provided by Aeromatic Fielder AG, DE) and mixed for 2 minutes in an upwards directed fluidising air flow of 25 m$^3$/h at a set temperature of 45° C. A granulation liquid is prepared by dissolving PVP (24 g, Povidone; provided by BASF, DE) and desmopressin acetate (0.80 g; provided by PolyPeptide Laboratories AB, SE) in water (80 g). The granulation liquid is then sprayed downwards at a constant rate during 15 minutes onto the lactose/starch mixture while the latter is simultaneously subjected to an upwards directed fluidising air flow of 25 m$^3$/h at a temperature of 45° C. When all the granulation liquid is added the same air flow and temperature is maintained for a further 20 minutes. The obtained dry granulate is then sieved (1.0 mm) and mixed with powdered magnesium stearate (4 g, 1.0 mm sieved; provided by Peter Greven NV, NL) for 2 minutes in a conventional mixer (AR400E; provided by EWREKA GmbH, DE), and subsequently compressed to 4000 tablets in a rotary punch (φ 8 mm) compression machine (Korsch XL 100; provided by Korsch, DE.) with a target weight of 200 mg. Tablets with a hardness of 5 kp (1 kp=9.81 N) and each containing 0.2 mg of desmopressin acetate were prepared in this manner. The tablets had a smooth surface without scratches or chipped edges, and no capping was observed.

All references listed are to be regarded as an integral part of the present writ.

The invention claimed is:

1. A method for the preparation of a solid dosage form of desmopressin acetate, comprising:
    (a) providing a powder comprising at least one excipient, carrier or diluent, or mixture thereof;
    (b) providing a granulation liquid comprising a solvent, a binder, and desmopressin acetate, and
    (c) contacting said granulation liquid with said powder within a fluid bed granulation apparatus and selecting fluidising air flow and processing temperature and time to provide mixing and shearing action to form a granulate, wherein said granulate is suitable for compression to a pharmaceutically acceptable tablet, and
    wherein said method provides a solid dosage form comprising an amount of desmopressin acetate of from 20 to 600 μg per unit.

2. The method according to claim 1, wherein said solvent is water.

3. The method according to claim 1, wherein said fluidising air flow is in the range of from 10 to 2500 m$^3$/h.

4. The method according to claim 1, wherein said processing temperature is in the range of from 25 to 80° C.

5. The method according to claim 1, wherein said processing time is in the range of from 10 to 240 minutes.

6. The method according to claim 1, wherein said excipient, carrier or diluent is selected from the group consisting of cellulose, starch and lactose.

7. The method according to claim 1, further comprising the step of compressing said granulate to a tablet.

8. The method according to claim 1, wherein the granulation liquid contains water as the sole solvent.

9. The method according to claim 3, wherein said fluidising air flow is in the range of from 20 to 1500 m$^3$/h.

10. The method according to claim 4, wherein said processing temperature is in the range of from 30 to 60° C.

11. The method according to claim 7, wherein a lubricant is added to said granulate prior to said compressing step.

12. The method according to claim 1, wherein said binder comprises PVP.

13. The method according to claim 1, wherein said lubricant is magnesium stearate.

14. The method according to claim 1, wherein said method provides a solid dosage form comprising an amount of desmopressin acetate of from 20 to 600 μg per unit.

* * * * *